(12) United States Patent
Peppel

(10) Patent No.: US 7,114,701 B2
(45) Date of Patent: Oct. 3, 2006

(54) NEEDLELESS ACCESS PORT VALVES

(75) Inventor: Peter W. Peppel, Nazareth, PA (US)

(73) Assignee: B. Braun Medical, Inc., Bethlehem, PA (US)

( * ) Notice: Subject to any disclaimer, the term of this patent is extended or adjusted under 35 U.S.C. 154(b) by 57 days.

(21) Appl. No.: 11/070,518

(22) Filed: Mar. 2, 2005

(65) Prior Publication Data

US 2006/0197045 A1    Sep. 7, 2006

(51) Int. Cl.
*F16K 51/00* (2006.01)
*A61M 5/00* (2006.01)

(52) U.S. Cl. .................. 251/149; 604/249; 604/256

(58) Field of Classification Search .............. 251/149, 251/149.1, 149.6; 604/45, 246, 249, 256, 604/537
See application file for complete search history.

(56) References Cited

U.S. PATENT DOCUMENTS

| | | | |
|---|---|---|---|
| 4,197,848 A | 4/1980 | Garrett et al. | |
| 4,535,819 A | 8/1985 | Atkinson et al. | |
| 4,765,588 A | 8/1988 | Atkinson | |
| 4,934,655 A | 6/1990 | Blenkush et al. | |
| 4,953,594 A | 9/1990 | Von Berg | |
| 5,006,114 A | 4/1991 | Rogers et al. | |
| 5,049,128 A | 9/1991 | Duquette | |
| 5,062,836 A * | 11/1991 | Wendell ............... | 604/249 |
| 5,065,783 A | 11/1991 | Ogle, II | |
| 5,104,389 A | 4/1992 | Deem et al. | |
| 5,108,380 A | 4/1992 | Herlitze et al. | |
| 5,147,333 A | 9/1992 | Raines | |
| 5,163,922 A | 11/1992 | McElveen, Jr. et al. | |
| 5,180,373 A * | 1/1993 | Green et al. ............ | 251/149.1 |
| 5,203,775 A | 4/1993 | Frank et al. | |
| 5,230,706 A | 7/1993 | Duquette | |
| 5,242,393 A | 9/1993 | Brimhall et al. | |
| 5,242,423 A | 9/1993 | Goodsir et al. | |
| 5,251,873 A | 10/1993 | Atkinson et al. | |
| 5,261,895 A * | 11/1993 | Kablik ............... | 604/249 |
| 5,269,771 A | 12/1993 | Thomas et al. | |
| 5,281,206 A | 1/1994 | Lopez | |
| 5,289,849 A | 3/1994 | Paradis | |
| 5,330,450 A | 7/1994 | Lopez | |
| 5,344,414 A | 9/1994 | Lopez et al. | |
| 5,353,837 A | 10/1994 | Faust | |
| 5,356,394 A * | 10/1994 | Farley et al. ............ | 604/256 |
| 5,360,413 A | 11/1994 | Leason et al. | |
| 5,380,306 A | 1/1995 | Brinon | |
| 5,390,898 A | 2/1995 | Smedley et al. | |
| 5,391,154 A * | 2/1995 | Young ................ | 251/149.1 |
| 5,395,348 A | 3/1995 | Ryan | |
| 5,401,245 A | 3/1995 | Haining | |
| 5,423,791 A | 6/1995 | Bartlett | |
| 5,425,465 A | 6/1995 | Healy | |
| 5,439,451 A | 8/1995 | Collinson et al. | |
| 5,441,487 A | 8/1995 | Vedder | |

(Continued)

*Primary Examiner*—John Bastianelli
(74) *Attorney, Agent, or Firm*—Christie, Parker & Hale, LLP

(57) ABSTRACT

Needleless access port valves are generally discussed herein with particular discussions extended to needleless access port valves comprising a resilient valve body. The resilient valve body includes a tapered set port that stretches when a plug is pushed by a medical implement which in turn pushes the set port. Pushing the plug against the set port opens fluid communication between the inlet port and the outlet port. Upon removal of the medical implement, the resilient valve body pushes the plug back to its closed position.

25 Claims, 2 Drawing Sheets

U.S. PATENT DOCUMENTS

| | | | |
|---|---|---|---|
| 5,462,255 | A | 10/1995 | Rosen et al. |
| 5,466,219 | A | 11/1995 | Lynn et al. |
| 5,509,433 | A | 4/1996 | Paradis |
| 5,509,912 | A | 4/1996 | Vaillancourt et al. |
| 5,533,983 | A | 7/1996 | Haining |
| 5,535,771 | A | 7/1996 | Purdy et al. |
| 5,535,785 | A | 7/1996 | Werge et al. |
| 5,540,661 | A | 7/1996 | Tomisaka et al. |
| 5,549,577 | A | 8/1996 | Siegel et al. |
| 5,569,235 | A | 10/1996 | Ross et al. |
| 5,573,516 | A | 11/1996 | Tyner |
| 5,584,808 | A | 12/1996 | Healy |
| 5,616,129 | A | 4/1997 | Mayer |
| 5,620,434 | A | 4/1997 | Brony |
| 5,624,414 | A | 4/1997 | Boettger |
| 5,645,538 | A | 7/1997 | Richmond |
| 5,674,206 | A | 10/1997 | Allton et al. |
| 5,676,346 | A | 10/1997 | Leinsing |
| 5,685,866 | A | 11/1997 | Lopez |
| 5,690,612 | A | 11/1997 | Lopez et al. |
| 5,694,686 | A | 12/1997 | Lopez |
| 5,695,466 | A | 12/1997 | Lopez et al. |
| 5,699,821 | A | 12/1997 | Paradis |
| 5,700,248 | A | 12/1997 | Lopez |
| 5,730,418 | A | 3/1998 | Feith et al. |
| 5,738,663 | A | 4/1998 | Lopez |
| 5,743,894 | A | 4/1998 | Swisher |
| 5,776,113 | A | 7/1998 | Daugherty et al. |
| 5,782,816 | A | 7/1998 | Werschmidt et al. |
| 5,785,693 | A | 7/1998 | Haining |
| 5,788,215 | A | 8/1998 | Ryan |
| 5,806,551 | A | 9/1998 | Meloul et al. |
| 5,806,831 | A | 9/1998 | Paradis |
| 5,810,768 | A | 9/1998 | Lopez |
| 5,810,792 | A | 9/1998 | Fangrow, Jr. et al. |
| 5,810,793 | A | 9/1998 | Boettger |
| 5,839,715 | A | 11/1998 | Leinsing |
| 5,848,994 | A | 12/1998 | Richmond |
| 5,873,862 | A | 2/1999 | Lopez |
| 5,901,942 | A | 5/1999 | Lopez |
| 5,921,264 | A | 7/1999 | Paradis |
| 5,921,419 | A | 7/1999 | Niedospial, Jr. et al. |
| 5,928,204 | A | 7/1999 | Lopez |
| 5,957,898 | A | 9/1999 | Jepson et al. |
| 5,967,490 | A | 10/1999 | Pike |
| 5,971,950 | A | 10/1999 | Lopez et al. |
| 6,019,748 | A | 2/2000 | Lopez |
| 6,029,946 | A | 2/2000 | Doyle |
| 6,036,171 | A | 3/2000 | Weinheimer et al. |
| 6,039,302 | A | 3/2000 | Cote, Sr. et al. |
| 6,045,534 | A | 4/2000 | Jacobsen et al. |
| 6,063,062 | A | 5/2000 | Paradis |
| 6,068,011 | A | 5/2000 | Paradis |
| 6,083,194 | A | 7/2000 | Lopez |
| 6,106,502 | A | 8/2000 | Richmond |
| 6,113,068 | A | 9/2000 | Ryan |
| 6,117,114 | A | 9/2000 | Paradis |
| 6,127,320 | A | 10/2000 | van Ooij et al. |
| 6,132,403 | A | 10/2000 | Lopez |
| 6,132,404 | A | 10/2000 | Lopez |
| 6,142,446 | A | 11/2000 | Leinsing |
| 6,168,137 | B1 | 1/2001 | Paradis |
| 6,170,800 | B1 | 1/2001 | Meloul et al. |
| 6,171,287 | B1 | 1/2001 | Lynn et al. |
| 6,189,859 | B1 | 2/2001 | Rohrbough et al. |
| 6,228,069 | B1 | 5/2001 | Barth et al. |
| 6,245,048 | B1 | 6/2001 | Fangrow, Jr. et al. |
| 6,245,056 | B1 | 6/2001 | Walker et al. |
| 6,261,282 | B1 | 7/2001 | Jepson et al. |
| 6,273,869 | B1 | 8/2001 | Vaillancourt |
| 6,290,206 | B1 | 9/2001 | Doyle |
| 6,290,688 | B1 | 9/2001 | Lopez et al. |
| 6,299,131 | B1 | 10/2001 | Ryan |
| 6,299,132 | B1 | 10/2001 | Weinheimer et al. |
| 6,325,782 | B1 | 12/2001 | Lopez |
| 6,344,033 | B1 | 2/2002 | Jepson et al. |
| 6,364,869 | B1 | 4/2002 | Bonaldo |
| 6,428,520 | B1 | 8/2002 | Lopez et al. |
| 6,482,188 | B1 | 11/2002 | Rogers et al. |
| 6,491,668 | B1 | 12/2002 | Paradis |
| 6,541,802 | B1 | 4/2003 | Doyle |
| 6,572,592 | B1 | 6/2003 | Lopez |
| 6,585,229 | B1 | 7/2003 | Cote, Sr. et al. |
| 6,599,273 | B1 | 7/2003 | Lopez |
| 6,616,627 | B1 | 9/2003 | Willis et al. |
| 6,626,418 | B1 | 9/2003 | Kiehne |
| 6,635,044 | B1 | 10/2003 | Lopez |
| 6,641,561 | B1 | 11/2003 | Hill et al. |
| 6,645,170 | B1 | 11/2003 | Landau |
| 6,669,673 | B1 | 12/2003 | Lopez |
| 6,669,681 | B1 | 12/2003 | Jepson et al. |
| 6,682,509 | B1 | 1/2004 | Lopez |
| 6,695,817 | B1 | 2/2004 | Fangrow, Jr. |
| 6,706,022 | B1 | 3/2004 | Leinsing et al. |
| 6,755,391 | B1 | 6/2004 | Newton et al. |
| 6,758,833 | B1 | 7/2004 | Lopez |
| 6,802,490 | B1 | 10/2004 | Leinsing et al. |
| 6,840,501 | B1 | 1/2005 | Doyle |
| 6,855,138 | B1 | 2/2005 | Tsai |
| 6,869,426 | B1 | 3/2005 | Ganem |
| 6,871,838 | B1 | 3/2005 | Raines et al. |

* cited by examiner

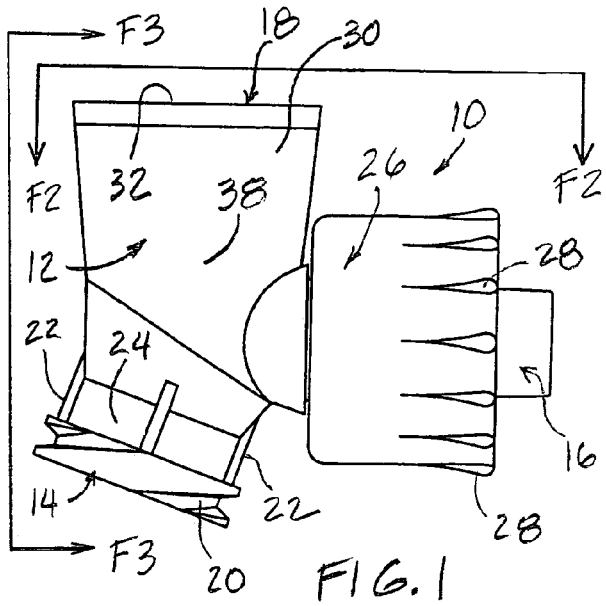
FIG. 1
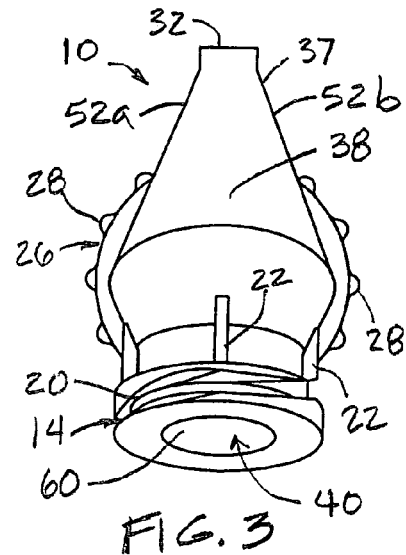
FIG. 3
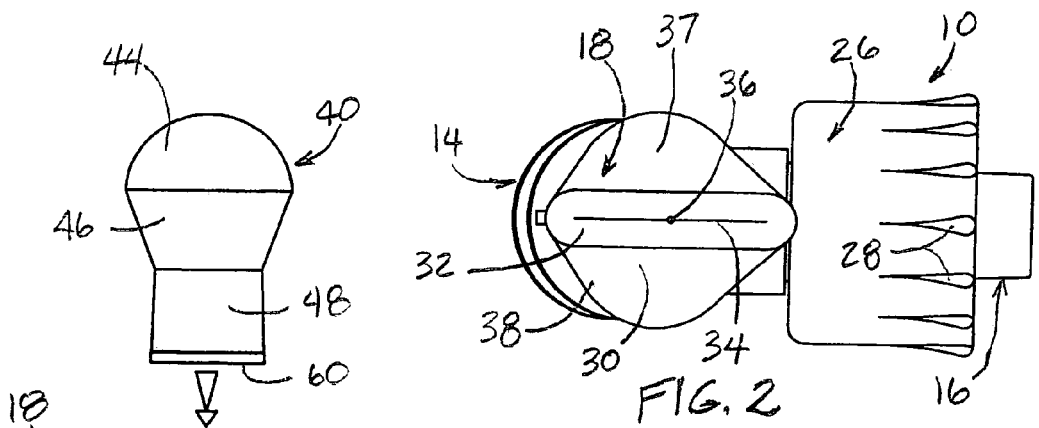
FIG. 2
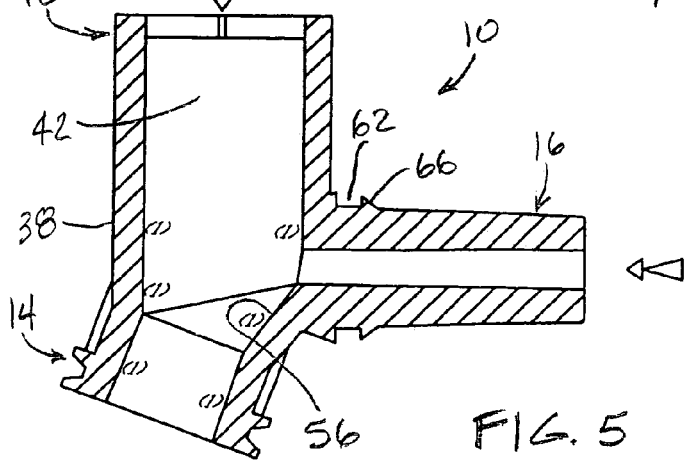
FIG. 5
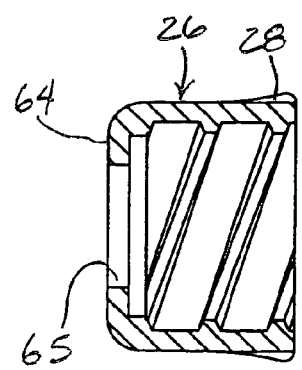

NEEDLELESS ACCESS PORT VALVES

Needleless access port valves are generally discussed herein with particular discussions extended to needleless access port valves comprising a resilient valve body.

BACKGROUND

Needleless access port valves are widely used in the medical industry for accessing an IV line and/or the internals of a patient or subject. Generally speaking, prior art valves utilize a valve housing in combination with a moveable internal plug or piston to control the flow of fluid through a valve. The plug or piston may be moved by a syringe or a medical implement to open the inlet of the valve for accessing the interior cavity of the valve. When a fluid is delivered through the valve, fluid flow typically flows around the outside of the plug or piston in the direction towards the outlet. Upon removal of the syringe or medical implement, the plug or piston returns to its original position, either un-aided or aided by a biasing means, such as a spring or a diaphragm.

In some prior art valves, when the syringe or medical implement pushes the plug or piston, the plug or piston is pierced by a piercing device, such as a spike. The spike typically incorporates one or more fluid channels for fluid flow flowing through the pierced piston and then through the fluid channels in the spike. In yet other prior art valves, a self-flushing or positive flush feature is incorporated to push residual fluids confined inside the interior cavity of the valve to flow out the outlet when the syringe or medical implement is removed.

While prior art needleless access port valves are viable options for their intended applications, there remains a need for alternative needleless access port valves.

SUMMARY

The present invention may be implemented by providing a needleless access port valve comprising a valve body, an inlet port, an outlet port, a set port comprising a squeezed end comprising a sealed seam, and a plug moveable from between the inlet port and the set port for allowing fluid communication between the inlet port and the outlet port.

In another aspect of the present invention, there is provided a needleless access port valve comprising a valve body, an inlet port, an outlet port, a set port comprising a seam and a taper surface that tapers radially outwardly as it extends towards the inlet port, and a plug comprising a dome, a first position, and a second position; wherein the dome abuts the taper surface of the set port when the plug is in the second position.

In yet another aspect of the present invention, there is provided a needleless access port valve comprising a valve body, an inlet port, an outlet port, a set port comprising a seam and a vent hole, a collar matingly engaged to the outlet port, and a plug operatively moveable by a medical implement to permit fluid communication between the inlet port and the outlet port.

In yet another aspect of the present invention, a two part self-lubricating material may be used to form a plug, or at least part, of the plug for facilitating movement of the plug inside the valve body.

In still yet another aspect of the present invention, there is provided an integrally formed inlet port, outlet port, and set port.

BRIEF DESCRIPTION OF THE DRAWINGS

These and other features and advantages of the present invention will become appreciated as the same become better understood with reference to the specification, claims and appended drawings wherein:

FIG. 1 is a semi-schematic side view of a needleless access port valve provided in accordance with aspects of the present invention;

FIG. 2 is a semi-schematic top view of the valve of FIG. 1 taken along line F2—F2;

FIG. 3 is a semi-schematic side view of the valve of FIG. 1 taken along line F3—F3;

FIG. 5 is a semi-schematic exploded cross-sectional side view of the valve of FIG. 1 prior to assembly.

DETAILED DESCRIPTION

Figure 4:
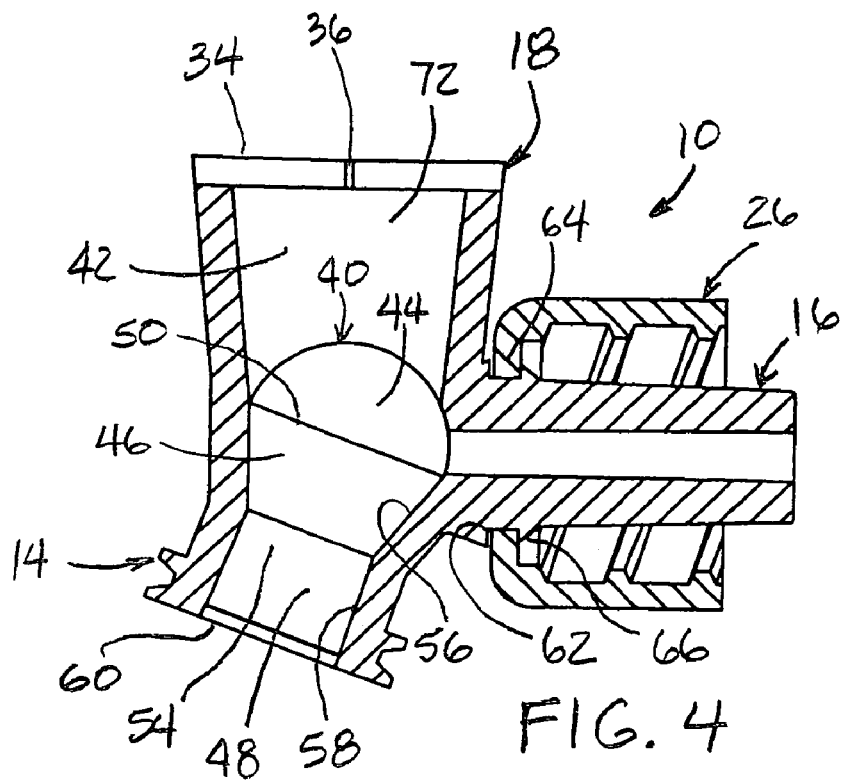
FIG. 4 is a semi-schematic cross-sectional side view of the valve of FIG. 1 taken along the same viewing plane.

The detailed description set forth below in connection with the appended drawings is intended as a description of the presently preferred embodiments of needleless access port valves or backcheck valves (herein "valves") provided in accordance with aspects of the present invention and is not intended to represent the only forms in which the present invention may be constructed or utilized. The description sets forth the features and the steps for constructing and using the valves of the present invention in connection with the illustrated embodiments. It is to be understood, however, that the same or equivalent functions and structures may be accomplished by different embodiments that are also intended to be encompassed within the spirit and scope of the invention. As denoted elsewhere herein, like element numbers are intended to indicate like or similar elements or features.

FIG. 1 is a semi-schematic side view of an exemplary valve provided in accordance with aspects of the present invention, which is generally designated 10. In one exemplary embodiment, the valve 10 comprises a valve body 12, an inlet port 14, an outlet port 16, and a set port 18. Preferably, the valve body 12 is integrally formed with the inlet, outlet, and set ports 14, 16, 18. More preferably, the components are integrally formed from a thermoplastic elastomer (TPE), which has, among other things, a resilient property. In one exemplary embodiment, the TPE is a member of the copolyamide (COPA) family of thermoplastic elastomers. In a preferred embodiment, the COPA is copolyamide thermoplastic elastomer having a commercial trade name PEBAX®. However, other TPEs may also be used to make the valve body 12, including thermoplastic polyurethanes (TPUs), styrenic thermoplastic elastomers, thermoplastic polyolefins (TPOs), copolyesters (COPEs), and thermoplastic vulcanizate elastomeric alloys (TPVs). Optionally, the TPEs may be cross-linked either chemically or by irradiation to alter their characteristics. In one exemplary embodiment, one or more colors are incorporated in the material. Preferably, the material has a translucent pantone green tone. Alternatively, an opaque material with one or more color tones or a clear finish may be incorporated.

In one exemplary embodiment, the inlet port 14 comprises an inlet female luer with threads 20. Preferably, a plurality of interference ribs 22 adorn an exterior surface 24 of the inlet port adjacent the threads 20 to provide an interference between the inlet port 14 and a corresponding threaded collar on a medical implement.

In one exemplary embodiment, the outlet port 16 is a male luer and is configured to mechanically couple to a collar 26 comprising a plurality of protrusions 28 for axial and rotational manipulation, as further discussed below. Preferably, the plurality of protrusions 28 are evenly spaced apart tear-drop-shape protrusions and the mechanical coupling between the collar 26 and the outlet port 16 comprises a detent coupling, as further discussed below. The collar preferably comprises threads (See FIG. 4) for threaded engagement with a medical implement. Although the collar 26 may be made from the same material as the valve body 12, in a preferred embodiment, the collar 26 is made from a rigid plastic, such as from polycarbonate, ABS, PEEK, SAN, etc.

The set port 18 comprises a generally cylindrical open-ended port for setting a plug (See FIG. 4), which is subsequently pinched and sealed closed, as further discussed below. The set port 18 comprises an exterior surface 30 and an interior surface. The set port may be sealed by pinching the end edge 32 of the set port 18 and applying adhesive to the interior surface. Alternatively, heat sealing may be used. Preferably, the set port 18 is sealed by pinching the end edge 32 and laser welding the seam using a diode laser. Once sealed, the set port resembles a mid-section of a pinched soda can.

FIG. 2 is a semi-schematic top view of the valve 10 of FIG. 1 taken along line F2—F2. A seam 34 is shown formed by pinching the set port 18 and sealing the interior surface. A vent hole 36 is incorporated along the seam 34 for venting gas inside the set port 18 during movement of a plug located inside the valve, as further discussed below. The vent hole 36 may be formed by molding an undercut or alternatively cutting the hole subsequent to sealing the seam 34.

Assuming the vent port 18 comprises a generally circular cross-section comprising a diameter prior to pinching and sealing the set port and the set port is aligned with respect to an X-axis parallel to the seam 34 and a Y-axis perpendicular to the seam 34, following the pinching and sealing process, the end edge 32 comprises a length defined by the X-axis and a width defined by the Y-axis. As is readily apparent to a person of ordinary skill in the art, the length of the end edge 32, measured from the exterior surface 30 of the set port, has a larger dimension than the diameter of the set port prior to being pinched. However, the width of the end edge 32 has a smaller dimension than the diameter of the set port prior to being pinched. The exterior surface 37 adjacent the width, therefore, tapers outwardly from the end edge 32 towards the main body section 38 of the valve and the inlet port 14. Hence, if a plug is pushed internally of the valve towards the set port 18, the plug will be squeezed by the exterior surface 37 along the Y-axis but not, or at least not substantially, along the X-axis. This squeezing action, as further discussed below, allows the set port to manipulate the plug back into its closed position.

FIG. 3 is a semi-schematic side view of the valve of FIG. 1 taken along line F3—F3. The taper exterior surface 37 is clearly shown, which tapers radially outwardly as it extends in the direction of the inlet port 14. While the taper exterior surface 37 of the set port 18 is orientated relative to the inlet port 14 and the collar 26, and hence the outlet port 16, as shown, the relative orientation can vary by varying the angular orientation of the seam 34 relative to the axis defined by the outlet port 16.

FIG. 4 is a semi-schematic cross-sectional side view of the valve 10 of FIG. 1 taken from the same viewing plane.

A plug 40 is shown disposed in the interior cavity 42 of the valve 10, in a closed or first position. In one exemplary embodiment, the plug 40 comprises a semi-spherical arc surface or dome section 44, a tapered mid-section 46, and a top section 48. A dome base 50 comprising a dome dimension is located at the transition between the dome section 44 and the mid-section 46 of the plug 40. Assuming that the taper exterior surface 37 of the set port has an infinite number of dimensions measured from between the two side surfaces 52a, 52b (FIG. 3) of the set port 18 along infinite numbers of planes perpendicular to the axis defined by the set port 18. Assuming also that the infinite number of dimensions are collectively referred to herein as a tapered dimension. The dome dimension is generally larger than the tapered dimension measured along any of the various planes. Due to the relative dimensions between the set port 18 and the plug 40, and more specifically between the tapered dimension and the dome dimension, a resilient force is therefore provided by the set port 18 when the same is pushed by the plug 40 and stretches, which produces a rebounding force acting the dome section 44 to push the plug 40 in the direction of the opening 54 of the inlet port 14. This resilient force causes the plug to close the opening 54 and terminate fluid communication between the inlet port 14 and the outlet port 16.

In an exemplary embodiment, the tapered mid-section 46 of the plug 40 is operatively pushed against a corresponding tapered surface 56 of the interior cavity 42 to seal the inlet port 14. Alternatively or in addition thereto, the base section 48 of the plug 40 is operatively pushed against a corresponding interior surface 58 of the inlet port 14 to seal the inlet port. More preferably, the seal is provided by the tapered mid-section 46 of the plug and the corresponding tapered surface 56 of the valve body while the base section 48 of the plug and the corresponding interior surface 58 of the inlet port 14 are merely in a close contact arrangement.

To facilitate cleaning and swabbing the valve, the plug 40 incorporates a generally flat or smooth top surface 60. The smooth top surface 60 is preferably approximately even or flushed with the end edge of the inlet port 14 when the plug is in the first position. In an alternative embodiment, a plurality of projections forming one or more fluid channels or grooves may be incorporated on the top surface 60 of the plug 40 for facilitating fluid flow flowing from between a medical implement and the outlet port 16, as further discussed below with reference to FIG. 6.

As previously discussed, the collar 26 mechanically couples to the outlet port 16 via a detent configuration. In an exemplary embodiment, the detent configuration is provided by forming a groove 62 on the exterior surface of the outlet port 14 and incorporating an end flange 64 comprising an opening 65 on the collar 26 to function as a tongue or male detent. As the outlet port 14 is resilient and pliable, the end flange 64 easily slips over the projection 66 on the outlet port 14 forming part of the groove 62. The plurality of protrusions 28 on the collar 26 allow the collar to be gripped, rotated, and otherwise manipulated when mounting the collar 26 to the outlet port 16.

FIG. 5 is a semi-schematic exploded cross-sectional side view of the valve 10 of FIG. 1, which shows the valve prior to assembly. In one exemplary embodiment, a medical grade silicone lubricant is applied to the interior surface of the valve body 38 prior to inserting the plug 40. In a preferred embodiment, the medical grade silicone lubricant is applied to the surfaces designated with the marking element (1). The lubricant facilitates movement of the plug 40 when the same is pushed by a medical implement to open the inlet port 14 and pushed by the tapered surface 37 of the set port 18 to close the inlet port. Alternatively, the plug 40 may be made entirely from a self-lubricating material, which exudes lubricants whenever manipulated or squeezed. In one exemplary embodiment, the self-lubricating material is a two-part self-lube liquid silicone rubber. The two-part self-lube silicone rubber is commercially available from Nusil Silicone Technology of Santa Barbara, Calif. Various aspects of the self-lube liquid silicone rubber are described in Ser. No. 10/407,001, filed Apr. 3, 2003, the contents of which are expressly incorporated herein by reference as if set forth in full. In an alternative embodiment, the self-lube material is over-molded to the plug 40. In the over-molded plug embodiment and in an embodiment in which medical grade silicone lubricant is applied to the plug, the plug is preferably made from a rigid plastic, which may include polycarbonate.

Figure 6:
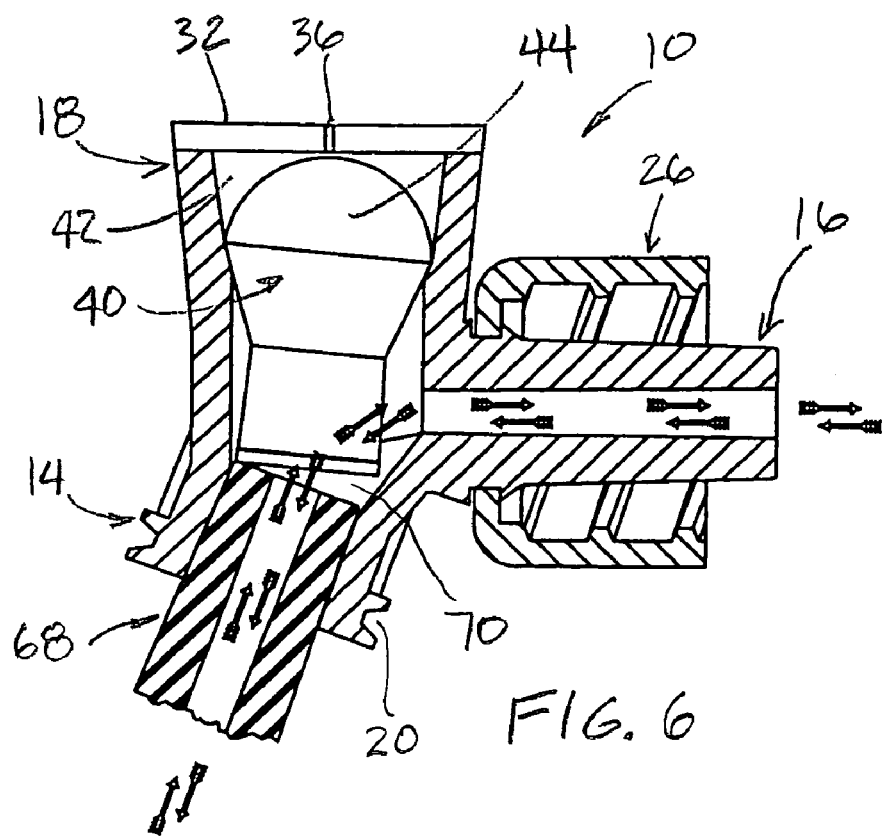
FIG. 6 is a semi-schematic cross-sectional side view of the valve of FIG. 1 in used with a medical implement.

FIG. 6 is a semi-schematic cross-sectional side view of the valve 10 of FIG. 1 in a used or plug second position. As shown, a medical implement 68, such as a syringe or an IV set, penetrates the opening 54 of the inlet port 14 and pushes the plug 40 in the direction of the set port 18. The displacement of the plug 40 causes the tapered surface 37 of the set port 18 to stretch, which causes a force to be applied on the dome section 44 of the plug 40 by the resilient material. As the plug 40 moves from a first position to a second position, gas in the in gas space 72 (FIG. 4) is pushed out the vent hole 36 located on the end edge 32 of the set port 18. However, it is possible to practice the valve disclosed herein without the vent hole.

Due to the contour of the internal cavity 42 of the valve, the plug 40 moves along a curved path when pushed by the medical implement 68 towards the set port 18. This in turn creates a gap 70 between the top surface 60 of the plug 40 and the end surface of the medical implement 68. The gap 70 provides fluid flow space for fluid flow from either the medical implement 68 towards the outlet port 16 or from the outlet port towards the medical implement.

Upon removal of the medical implement 68, the force generated by the stretched tapered surface 37 forces the plug 40 to return to its first position (FIG. 4). As the plug returns to its first position, gas is sucked back into the gas space 72 through the vent hole 36. Although a collar-less medical implement 68 is shown, the medical implement 68 may include a threaded collar, which would threadedly engage with the threads 20 on the inlet port for improved attachment between the two.

Although limited embodiments of the needleless access port valves and their components have been specifically described and illustrated herein, many modifications and variations will be apparent to those skilled in the art. For example, the various valves may incorporate luer-slips rather than luer threads, the material selected could be opaque or semi-opaque, different colors may be used, the dimensions can vary, etc. Accordingly, it is to be understood that the valve assemblies and their components constructed according to principles of this invention may be embodied other than as specifically described herein. The invention is also defined in the following claims.

What is claimed is:

1. A needleless access port valve comprising a valve body, an inlet port, an outlet port, a set port comprising a squeezed end comprising a sealed seam, and a plug moveable from between the inlet port and the set port for allowing fluid communication between the inlet port and the outlet port.

2. The needleless access port valve of claim 1, wherein the set port further comprises a vent hole.

3. The needleless access port valve of claim 1, wherein the set port tapers outwardly as it extends towards the inlet port.

4. The needleless access port valve of claim 1, wherein the valve is made from a thermoplastic elastomer.

5. The needleless access port valve of claim 1, further comprising a threaded collar engaged to the outlet port.

6. The needleless access port valve of claim 5, wherein the threaded collar is made from a rigid plastic material.

7. The needleless access port valve of claim 1, wherein the outlet port comprises a groove along an exterior surface for engaging an opening of a collar.

8. The needleless access port valve of claim 7, where the collar comprises a plurality of protrusions.

9. The needleless access port valve of claim 1, wherein the plug comprises a dome-shape section and a base section.

10. A needleless access port valve comprising a valve body, an inlet port, an outlet port, a set port comprising a seam and a taper surface that tapers radially outwardly as it extends towards the inlet port, and a plug comprising a dome, a first position, and a second position; wherein the dome abuts the taper surface when the plug is in the second position.

11. The needleless access port valve of claim 10, wherein the seam is heat welded.

12. The needleless access port valve of claim 10, wherein the seam is laser welded.

13. The needleless access port valve of claim 10, wherein the seam comprises a vent hole.

14. The needleless access port valve of claim 10, wherein the valve is made from a thermoplastic elastomer material.

15. The needleless access port valve of claim 10, further comprising a collar connected to an exterior surface of the outlet port.

16. The needleless access port valve of claim 15, wherein the collar engages the exterior surface in a tongue-and-groove arrangement.

17. The needleless access port valve of claim 16, wherein the collar comprises a plurality of threads.

18. The needleless access port valve of claim 10, wherein the outlet port comprises a male luer taper.

19. The needleless access port valve of claim 10, wherein the inlet comprises exterior threads.

20. A needleless access port valve comprising a valve body, an inlet port, an outlet port, a set port comprising a vent hole and a seam formed by a squeezed end, a collar matingly engaged to the outlet port, and a plug operatively moveable by a medical implement to permit fluid communication between the inlet port and the outlet port.

21. The needleless access port valve of claim 20, wherein the collar is engaged to the outlet port in a tongue-and-groove arrangement.

22. The needleless access port valve of claim 20, wherein the seam is sealed by heat welding.

23. The needleless access port valve of claim 20, wherein the seam is sealed by bonding.

24. The needleless access port valve of claim 20, wherein the inlet port comprises exterior threads.

25. The needleless access port valve of claim 20, wherein the valve is made from a thermoplastic elastomer material.

* * * * *